United States Patent
Friesz et al.

(10) Patent No.: US 9,701,654 B2
(45) Date of Patent: Jul. 11, 2017

(54) PROCESS FOR PREPARATION OF DRONEDARONE BY REMOVAL OF HYDROXYL GROUP

(71) Applicant: SANOFI, Paris (FR)

(72) Inventors: Antal Friesz, Budapest (HU); Zsolt Dombrády, Budapest (HU)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/946,510

(22) Filed: Nov. 19, 2015

(65) Prior Publication Data

US 2016/0075674 A1 Mar. 17, 2016

Related U.S. Application Data

(62) Division of application No. 14/376,605, filed as application No. PCT/HU2013/000010 on Feb. 1, 2013, now Pat. No. 9,221,778.

(30) Foreign Application Priority Data

Feb. 13, 2012 (EP) ..................................... 12462004

(51) Int. Cl.
C07D 307/80 (2006.01)
C07D 307/81 (2006.01)
C07D 407/12 (2006.01)

(52) U.S. Cl.
CPC ......... C07D 307/81 (2013.01); C07D 307/80 (2013.01); C07D 407/12 (2013.01)

(58) Field of Classification Search
CPC .................................................... C07D 307/80
See application file for complete search history.

(56) References Cited

U.S. PATENT DOCUMENTS

| | | |
|---|---|---|
| 3,577,441 A | 5/1971 | Kaminsky et al. |
| 3,657,350 A | 4/1972 | Mooradian et al. |
| 3,937,737 A | 2/1976 | Eiglmeier |
| 4,243,405 A | 1/1981 | Balasubramanyan et al. |
| 4,666,931 A | 5/1987 | Ohishi et al. |
| 5,066,803 A | 11/1991 | D'Ambra et al. |
| 5,223,510 A | 6/1993 | Gubin et al. |
| 6,555,697 B1 | 4/2003 | Schlama |
| 6,828,448 B2 | 12/2004 | Fino et al. |
| 6,846,936 B2 | 1/2005 | Biard |
| 6,855,842 B1 | 2/2005 | Schlama et al. |
| 6,949,583 B2 | 9/2005 | Assens et al. |
| 6,984,741 B2 | 1/2006 | Magerlein |
| 7,148,240 B2 | 12/2006 | Assens et al. |
| 7,312,345 B2 | 12/2007 | Gutman et al. |
| 7,517,876 B2 | 4/2009 | Klein et al. |
| 8,143,269 B2 | 3/2012 | Whitten et al. |
| 8,501,971 B2 | 8/2013 | Friesz et al. |
| 8,658,808 B2 | 2/2014 | Kretzschmar et al. |
| 8,658,809 B2 | 2/2014 | Friesz et al. |
| 8,674,121 B2 | 3/2014 | Kretzschmar et al. |
| 8,686,180 B2 | 4/2014 | Bon et al. |
| 8,748,636 B2 | 6/2014 | Bailly et al. |
| 8,796,489 B2 | 8/2014 | Bailly et al. |
| 8,816,103 B2 | 8/2014 | Friesz et al. |
| 8,871,956 B2 | 10/2014 | Bailly et al. |
| 8,884,033 B2 | 11/2014 | Bon et al. |
| 8,889,734 B2 | 11/2014 | Friesz et al. |
| 8,927,743 B2 | 1/2015 | Vishnu Newadkar et al. |
| 8,962,869 B2 | 2/2015 | Grimaud et al. |
| 9,024,046 B2 | 5/2015 | Friesz et al. |
| 9,174,958 B2 | 11/2015 | Friesz |
| 9,174,959 B2 | 11/2015 | Friesz et al. |
| 9,221,777 B2 | 12/2015 | Friesz |
| 9,221,778 B2 * | 12/2015 | Friesz .................. C07D 407/12 |

(Continued)

FOREIGN PATENT DOCUMENTS

| | | |
|---|---|---|
| CN | 101838252 A | 9/2010 |
| CN | 101993427 A | 3/2011 |

(Continued)

OTHER PUBLICATIONS

Abramenko et al. (1975). "Polymethine Dyes—Furo[2,3-g] Benzothiazole Derivatives," *Chemistry of Heterocyclic Compounds* 11:1361-1364.

Adams et al. (1951). "Quinone imides. IV. P-Quinone monosulfonimides," *Journal of the American Chemical Society* 73:1145-1149.

Adams et al. (1956). "Quinone Imides. XXXIX. Adducts of Quinone Monoimides and Conversion of Active Methylene Adducts to Benzofurans," *J. Am. Chem. Soc.* 78(3):658-663.

Alcaraz et al. (2004). "Novel N-Aryl and N-Heteroaryl Sulfamide Synthesis via Palladium Cross Coupling," *Organic Letters* 6(16):2705-2708.

(Continued)

*Primary Examiner* — Golam M M Shameem
(74) *Attorney, Agent, or Firm* — Morrison & Foerster LLP

(57) ABSTRACT

The invention relates to a novel process for preparation of dronedarone of formula (I) and pharmaceutically acceptable salts thereof the hydroxyl group is removed, and the obtained product is isolated and, if desired, converted into a pharmaceutically acceptable salt thereof.

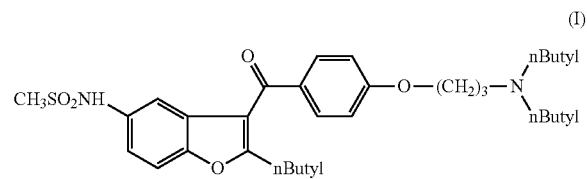

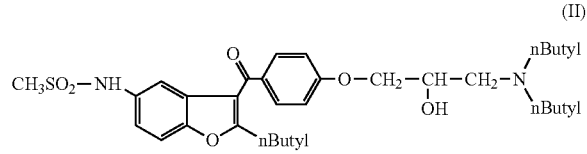

4 Claims, No Drawings

(56) References Cited

U.S. PATENT DOCUMENTS

| | | | |
|---|---|---|---|
| 9,238,636 | B2 | 1/2016 | Huszár et al. |
| 9,499,507 | B2 | 11/2016 | Bon et al. |
| 2008/0033209 | A1 | 2/2008 | Szarvas et al. |
| 2010/0273764 | A1 | 10/2010 | Andrews et al. |
| 2013/0023678 | A1 | 1/2013 | Priem et al. |
| 2014/0018553 | A1 | 1/2014 | Grimaud et al. |
| 2014/0081035 | A1 | 3/2014 | Friesz et al. |
| 2015/0005515 | A1 | 1/2015 | Friesz et al. |
| 2015/0018568 | A1 | 1/2015 | Friesz |
| 2015/0031901 | A1 | 1/2015 | Bon et al. |
| 2015/0031902 | A1 | 1/2015 | Huszar et al. |
| 2015/0274688 | A1 | 10/2015 | Huszar et al. |
| 2016/0009678 | A1 | 1/2016 | Huszár et al. |
| 2016/0009679 | A1 | 1/2016 | Friesz et al. |
| 2016/0075673 | A1 | 3/2016 | Friesz et al. |

FOREIGN PATENT DOCUMENTS

| | | | |
|---|---|---|---|
| EP | 0 471 609 A1 | | 2/1992 |
| EP | 0 735 083 A1 | | 10/1996 |
| FR | 2 833 259 A1 | | 6/2003 |
| GB | 1064959 A | | 4/1967 |
| WO | WO-96/05190 A1 | | 2/1996 |
| WO | WO-02/48078 A1 | | 6/2002 |
| WO | WO-02/48132 A1 | | 6/2002 |
| WO | WO-03/040120 A1 | | 5/2003 |
| WO | WO-2005/012301 A1 | | 2/2005 |
| WO | WO-2007/022501 A2 | | 2/2007 |
| WO | WO-2007/022501 A3 | | 2/2007 |
| WO | WO-2007/100295 A1 | | 9/2007 |
| WO | WO-2007/116111 A1 | | 10/2007 |
| WO | WO-2007/133637 A2 | | 11/2007 |
| WO | WO-2007/133637 A3 | | 11/2007 |
| WO | WO-2007/140989 A2 | | 12/2007 |
| WO | WO-2007/140989 A3 | | 12/2007 |
| WO | WO-2009/044143 A2 | | 4/2009 |
| WO | WO-2009/044143 A3 | | 4/2009 |
| WO | WO-2010/038029 A1 | | 4/2010 |
| WO | WO-2010/040261 A1 | | 4/2010 |
| WO | WO-2010/116140 A1 | | 10/2010 |
| WO | WO-2010/136500 A1 | | 12/2010 |
| WO | WO-2010/136502 A1 | | 12/2010 |
| WO | WO-2011/070380 A1 | | 6/2011 |
| WO | WO-2011/099010 A1 | | 8/2011 |
| WO | WO-2011/104591 A1 | | 9/2011 |
| WO | WO-2011/107705 A1 | | 9/2011 |
| WO | WO-2011/158050 A1 | | 12/2011 |
| WO | WO-2012/004658 A2 | | 1/2012 |
| WO | WO-2012/004658 A3 | | 1/2012 |
| WO | WO-2012/010788 A1 | | 1/2012 |
| WO | WO-2012/010802 A1 | | 1/2012 |
| WO | WO-2012/010913 A1 | | 1/2012 |
| WO | WO-2012/032545 A1 | | 3/2012 |
| WO | WO-2012/127173 A1 | | 9/2012 |
| WO | WO-2012/131408 A1 | | 10/2012 |
| WO | WO-2012/131409 A1 | | 10/2012 |
| WO | WO-2012/131410 A1 | | 10/2012 |
| WO | WO-2013/014478 A1 | | 1/2013 |
| WO | WO-2013/014479 A1 | | 1/2013 |
| WO | WO-2013/014480 A1 | | 1/2013 |
| WO | WO-03/048144 A2 | | 6/2013 |
| WO | WO-03/048144 A3 | | 6/2013 |
| WO | WO-2013/121234 A1 | | 8/2013 |
| WO | WO-2013/121235 A2 | | 8/2013 |
| WO | WO-2013/121235 A3 | | 8/2013 |
| WO | WO-2013/128294 A2 | | 9/2013 |
| WO | WO-2013/128294 A3 | | 9/2013 |
| WO | WO-2013/128294 A8 | | 9/2013 |

OTHER PUBLICATIONS

Ando et al. (1982). "Motion at the Active Site of Tosylchymotrypsin," *Journal of the American Chemical Society* 104(11):3172-3178.

Anjanappa et al. (2008). "2-(Trimethylsilyl)ethanesulfonyl amide as a new ammonia equivalent for palladium-catalyzed amination of aryl halides," *Tetrahedron Letters* 49:4585-4587.

Bartoli et al. (1991). "Unexpected Elimination to α,β-Alkynylketones in the Reaction of Dianions of 1-Arylenaminones with Trimethylchlorosilane," *Tetrahedron Letters* 32(48):7091-7092.

Batra et al. (2001). "Syntheses and Biological Evaluation of Alkanediamines as Antioxidant and Hypolipidemic Agents," *Bioorganic & Medicinal Chemistry* 9(12):3093-3099.

Bavin (1973). "2-Aminofluorene," *Org. Syn. Coll.* 5:30.

Berthold et al. (2002). "Transfer Hydrogenation in Ionic Liquids under Microwave Irradiation," *Syn.* 1607-1610.

Boovanahalli et al. (2004). "Application of Ionic Liquid Halide Nucleophilicity for the Cleavage of Ethers: A Green Protocol for the Regeneration of Phenols from Ethers," *Journal of Organic Chemistry* 69:3340-3344.

Bourgery et al. (1981). "Synthesis and Antiarrhythmic Activity of New Benzofuran Derivatives," *Journal of Medicinal Chemistry* 24(2):159-167.

Burton et al. (2003). "Palladium-Catalyzed Intermolecular Coupling of Aryl Chlorides and Sulfonamides under Microwave Irradiation," *Organic Letters* 5(23):4373-4376.

Castellino et al. (1984). "Synthesis of Benzofurans from Oxygenated Phenoxyamines," *Journal of Organic Chemistry* 49:4399-4404.

Chauhan et al. (2004). "Microwave assisted dealkylation of alkyl aryl ethers in ionic liquids," *Journal of Chemical Research*, pp. 693-694.

Cheng et al. (2007). "Facile Cleavage of Ethers in Ionic Liquid," *Bulletin of the Chemical Society of Japan* 80(10):2008-2010.

Database PubChem Compound [Online] (Oct. 25, 2006),"CID 10095002—Compound Summary:N-[3-[4-(3-aminopropoxy)benzoyl)-2-butyl-1-benzofuran-5-yl", XP002676507, Database accession No. 15082344. Retrieved from the Internet: URL:http://pubchem.ncbi.nlm.nih.gov/summary/summary.cgi?sid=15082344&viewopt=PubChem [retrieved on May 23, 2012].

Delahay et al. (2007). "Past and Recent Approaches of Preparing Fe-ZSM-5," *Current Topics in Catalysis* 6:19-33.

Douglass (1959). "Some New Reactions of Methanesulfenyl Chloride," *Journal of Organic Chemistry* 24:2004-2006.

Denmark et al. (2008). "Lewis base catalysis in organic synthesis," *Angew. Chem. Int. Ed.* 47(9):1560-1638.

Fehnel (1958). "Quinoline Analogs of Podophyllotoxin. I. Preliminary Experiments. Syntheses of Some 4-Phenylquinoline Derivatives," *J. Org. Chem.* 23:432-434.

Fieser et al. (1967). "Reagents for Organic Synthesis," John Wiley & Sons, pp. 703-705.

Fontana (2008). "Syntheses of (R,S)-Naproxen and its 6-O-Desmethyiated metabolite labelled with 2H," *J. Labelled Compounds and Radiopharma.* 51:239-241.

Gilow et al. (Jun.-Jul. 1991). "Sulfenylation of Some Pyrroles and Indoles," *J. Het. Chem.* 28:1025-1034.

Groves (1972). "The Friedel-Crafts Acylation of Alkenes," *Chem. Soc. Rev.* 1:73-97.

Gutowski et al, (2005). "Prediction of the Formation and Stabilities of Energetic Salts and Ionic Liquids Based on ab Initio Electronic Structure Calculations," *The Journal of Physical Chemistry B* 109:23196-23208.

Haddadin et al. (1976). "Reaction to Benzofurazan Oxide with Unsymmetrical 1, 3-Diketones: Steric Polar Effects," *Tetrahedron* 32:719-724.

Hauser et al. (1948) "Alkaline cleavage of unsymmetrical β-diketones. Ring opening of acylcyclohexanones to form ε-acylcaproic acids," *Journal of the American Chemical Society* 70:4023-4026.

Headley et al. (2006). "Dynamic Solvation in Imidazolium-Based Ionic Liquids on Short Time Scales," *Journal of Physical Chemistry* 110:9549-9554.

Horton et al. (1967). "Reactions With Reactive Alkyl Halides," *J. Meth. in Enzymology* 11:556-565.

(56) References Cited

OTHER PUBLICATIONS

Ikawa et al. (2007). "Pd-Catalyzed Amidations of Aryl Chlorides Using Monodentate Biaryl Phosphine Ligands: A Kinetic, Computational, and Synthetic Investigation," *Journal of the American Chemical Society* 129:13001-13007.
Imori et al. (2006). "Efficient Demethylation of N,N-Dimethylanilines with Phenyl Chloroformate in Ionic Liquids," *Synlett.* 16:2629-2632.
Johnson Matthey Handbook of Pharmaceutical Catalysis, 2009, pp. 1-106.
Joshi et al. (1986). "Some New Fluorinated β-Ketoamines and Their Copper Complexes," *Synth. React. Inorg. Met.—Org. Chem.* 16(7):1009-1024.
Krongauz et al. (1986). Poly(anilophenylquinoxaline)s. Inst. Elementoorg. Soedin. 28(4):771 (Abstract).
Kurti et al. (2005). Strategic Applications of Named Reactions in Organic Synthesis. *El Sevior,* pp. 448-449.
Kwiatkowski et al. (1978). "Metal Benzoylpivaloylmethanates, Part I. Free Ligands and Copper(II) Chelates," *Transition Met. Chem.* 3:305-308.
Laszlo et al. (1987). "Catalysis of Friedel-Crafts Alkylation by a Montmorillonite Doped with Transition-Metal Cations," *Helvetica Chimica Acta* 70:577-586.
Liu et al. (2004). "Cleavage of Methyl Ethers of Flavones by Chloroaluminate Ionic Liquid," *Synthetic Communications* 34:3209-3218.
Majdik (1985). "Studiul reactiei de ciclizare a orto-hidroxibenzilfenilcetonelor in benzofuran derivati," *Revista de Chimie* 36(8):760-761 (with English Translation).
Majdik et al. (1989). "Prepararea unor 2-(aril)-nitrobenzofurani din 0-(nitrofenil)-acetofenonoxime," *Revista de Chemie,* vol. 40, No. 8, pp. 689-693 (with English Translation).
Majdik et al. (1989). "0-Arilarea cetoximelor cu nitroclorbenzeni," *Revista de Chemie,* vol. 40, No. 6, pp. 490-493 (with English Translation).
March (Jul. 1, 1992). "Aromatic Electrophilic Substitution," Chapter 11 in *Advanced Organic Chemistry, Reactions, Mechanism and Structure,* 4th edition, Wiley Interscience, pp. 538-542.
March (Jul. 1, 1992). "Aliphatic Nucleophilic Substitution," Part 2 in *Advanced Organic Chemistry, Reactions, Mechanism and Structure,* 4th edition, Wiley Interscience, pp. 442.
Marvel et al. (1941). "Diphenylacetic Acid," *Org. Synth. Coll.* vol. 1, 224-225.
Mehrotra et al. (2001). "Search for new chemical entities as menses inducing agents," *Contraception* 64:187-191.
Munch et al. (1946). "The Preparation of Some α-Dialkylamino-ω-Methylaminoalkanes," *J. Am. Chem. Soc.* 68:1297-1299.
Nagy et al. (2007). "Isomorphous Substitution in Zeolites," *Mol. Sieves* 5:365-478.
Nakamura et al. (2004). "Pyrazole Derivatives as new potent and selective 20-hydroxy-5,6,11,14-Eicosatetraenoic Acid Synthase Inhibitors," *Bioorganic Medic. Chem.* 12:6209-6219.
Pal et al. (2007). "Synthesis of monohydroxy-functionalized triphenylene discotics: green chemistry approach," *Tetrahedron* 63:6874-6878.
Roshchin et al. (1998). "Synthesis of Benzofurans via Pd2+-Catalyzed Oxidative Cyclization of 2-Allylphenols," *Journal of Organometallic Chemistry* 560(1-2):163-167.
Sanfilippo (1988). "Synthesis of (aryloxy)alkylamines. 1. Novel antisecretory agents with H+K+-ATPase inhibitory activity," *J. Med. Chem.* 31(9):1778-1785.
Serajuddin (2007). "Salt formation to improve drug solubility," *Advanced Drug Delivery Reviews* 59:603-616.
Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," *Indian Journal of Chemistry* 208:234-237.
Skeels et al. (1989). "Zeolite Chemistry, Substitution of iron or titanium for Aluminum in Zeolites via reaction with the respective ammonium fluoride salts," *ACS Symposium Series, zeolite Synthesis* 398:420-435.
Ślusarska et al. (Feb. 1981). "One-Pot Phase-Transfer-Catalysed N-Alkylation of Diphenylphosphinamide with Alcohols in the Presence of Methanesulfonyl Chloride," *Synthesis* 155-156.
Son et al. (1989). "Stereochemical Mechanism of Iodoacetic Acid Mediated Decomposition of $_L$-Methionine to $_L$-Homoserine Lactone," *Journal of the American Chemical Society* 111(4):1363-1367.
Sun et al. (2004). "N-{2-[2-( 4-Phenylbutyl)benzofuran-4-yl]cyclopropylmethyl}-acetamide: an orally bioavailable melatonin receptor agonist," *Bioorganic & Medicinal Chemistry Letters* 14:5157-5160.
Tanaka (1967). "Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives," *Bulletin of the Chemical Society of Japan* 40(7):1724-1726.
Thornber (1979). "Isosterism and molecular modification in drug design." *Chem. Soc. Rev.* 8:563-580.
Upthagrove et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," *Drug Metab. Dispos.* 29(11):1377-1388.
Wamser et al. (1989). "Kinetics and Mechanisms for the Two-phase Reaction between Aqueous Aniline and Benzoyl Chloride in Chloroform, with and without Pyridine Catalysis," *J. Org. Chem.* 54:150-154.
Weissman et al. (2005). "Recent advances in ether dealkylation," *Tetrahedron* 61:7833-7863.
Weitkamp et al. (1986). "Isomorphe Substitution in Zeolithen: Katalyse an Boro-, Alumo-und Galio-Silicaten mit ZSM-5-Strukter," *Chem. Ing. Tech.* 58(12):969-971 (with English Translation).
Wikipedia. (Nov. 5, 2012). "Reduction of Nitro Compounds."
Wu et al. (2004). "Immobilization of HX: [Hmim]X as Halogenating Agent, Recyclable Catalyst and Medium for Conversion of Alcohols to alkyl halides," *Chinese J. Chem.* 22:619-621.
Wuts (2006). Greene's Protective Groups in Organic Synthesis, Fourth Edition, John Wiley and Sons, Chapter 7, Protection for the Amino Group, pp. 696-926.
Yang et al. (2009). "Structure-based virtual screening for identification of novel 11 β-HSD1 inhibitors," *European J. of Medicinal Chem.* 44(3):1167-1171.
Yin et al. (2000). "Palladium-Catalyzed Intermolecular Coupling of Aryl Halides and Amides," *Organic Letters* 2(8):1101-1104.
Yin et al. (2002). "Pd-Catalyzed Intermolecular Amidation of Aryl Halides: The Discovery that Xantphos Can Be Trans-Chelating in a Palladium Complex," *Journal of the American Chemical Society* 124:6043-6048.
Zasshi (1956). "Studies on the Syntheses of Phenothiazine Derivatives. I. Syntheses of N-Substituted Phenothiazines by Tosylates," *J. Pharm. Soc. of Japan* 76:637-640 (with English Translation).
U.S. Appl. No. 14/377,484, filed Aug. 7, 2014, by Huszar et al.
U.S. Appl. No. 14/863,206, filed Sep. 23, 2015, by Friesz et al.
U.S. Appl. No. 14/945,222, filed Nov. 18, 2015, by Friesz et al.
Landge, S.B. et al. (2013; e-published on Jun. 2013). "Stability Indicating RP-HPLC Method for the Determination of Dronedarone Hydrochloride and its Potential Process-Related Impurities in Bulk Drug and Pharmaceutical Dosage Form," *American Journal of Analytical Chemistry* 4:323-335.
Li et al. (2011) "Synthesis of Dronedarone Hydrochloride," *Chinese Journal of Pharmaceuticals* 42(3):161-164, (English abstract only).
Stahl, P.H. et al. (2005). "List of Pharmaceutically Acceptable Acids," The Royal Society of Chemistry in *Handbook of Pharmaceutical Salts: Properties, Selection and Use,* Electronic Supplementary Material for CrystEngComm, one page.

* cited by examiner

PROCESS FOR PREPARATION OF DRONEDARONE BY REMOVAL OF HYDROXYL GROUP

CROSS-REFERENCE TO RELATED APPLICATIONS

This application is a divisional patent application of U.S. patent application Ser. No. 14/376,605, which adopts the international filing date of Feb. 1, 2013, which is a National Phase application under 35 U.S.C. §371 of International Application No. PCT/HU2013/000010, filed Feb. 1, 2013, which claims priority benefit to EP Application No. 12462004.8, filed Feb. 13, 2012, the disclosures of each of which are incorporated herein by reference in their entireties.

FIELD OF THE INVENTION

This invention relates to a novel process for the preparation of dronedarone and pharmaceutically acceptable salts thereof, to novel intermediary compounds used in this process and their preparation.

TECHNICAL BACKGROUND

Dronedarone is a known drug for the treatment of arrhythmia and has the chemical name of N-[2-n-butyl-3-[4-[3-(di-n-butylamino)propoxy]benzoyl]benzofuran-5-yl]methane-sulfon-amide [see also formula (I) below]. There are some known processes for the preparation of dronedarone as follows:

In EP 0471609 the following scheme is disclosed for the preparation of dronedarone [Process A]

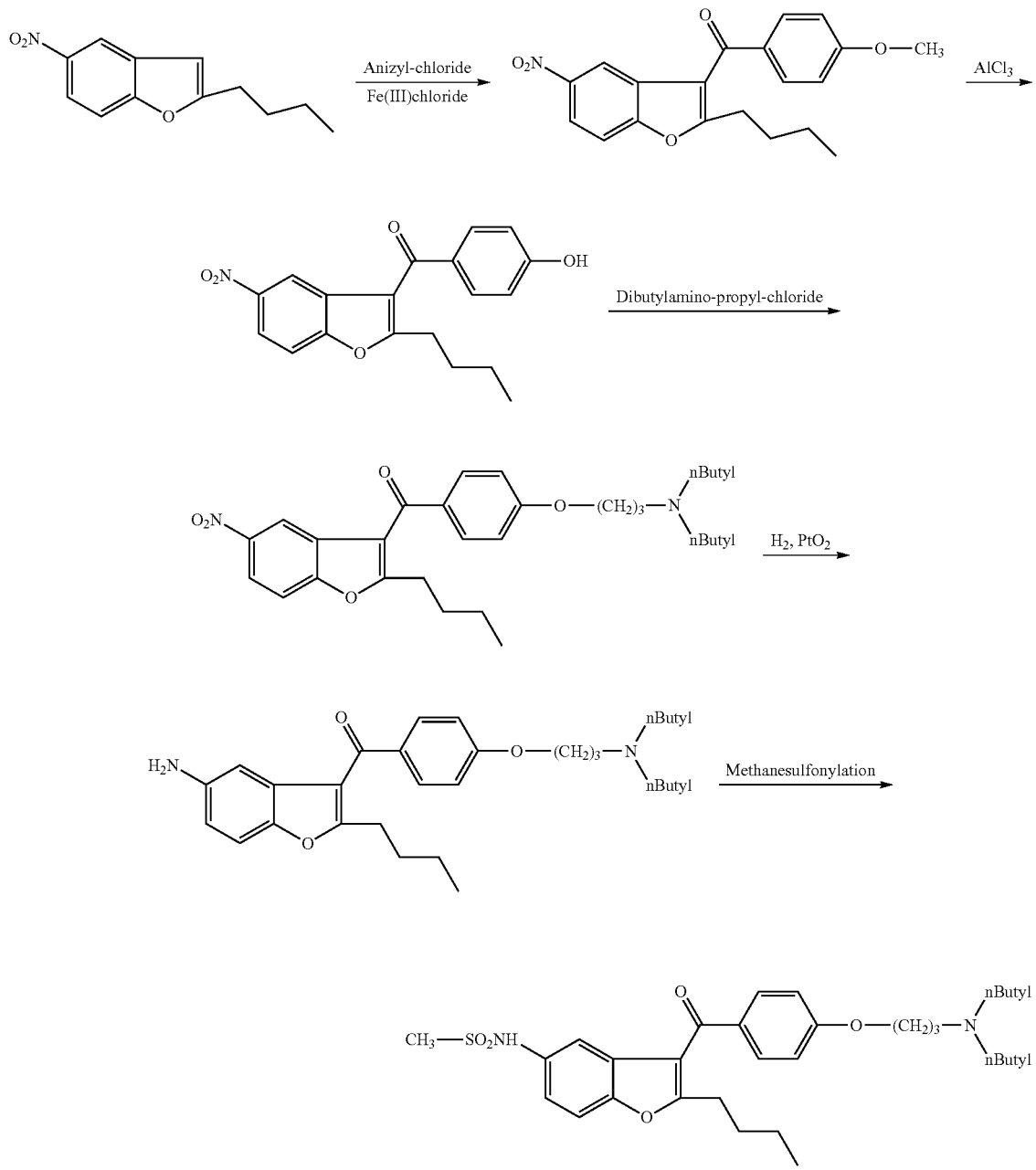

The above mentioned patent description discloses some new intermediary compounds, too.

In WO 02/48078 the following scheme is disclosed for the preparation of dronedarone [Process B]:

is mesylated and the obtained 2-butyl-5-methanesulfonamido-benzofuran (in HCl salt form) is further reacted in the next step as follows:

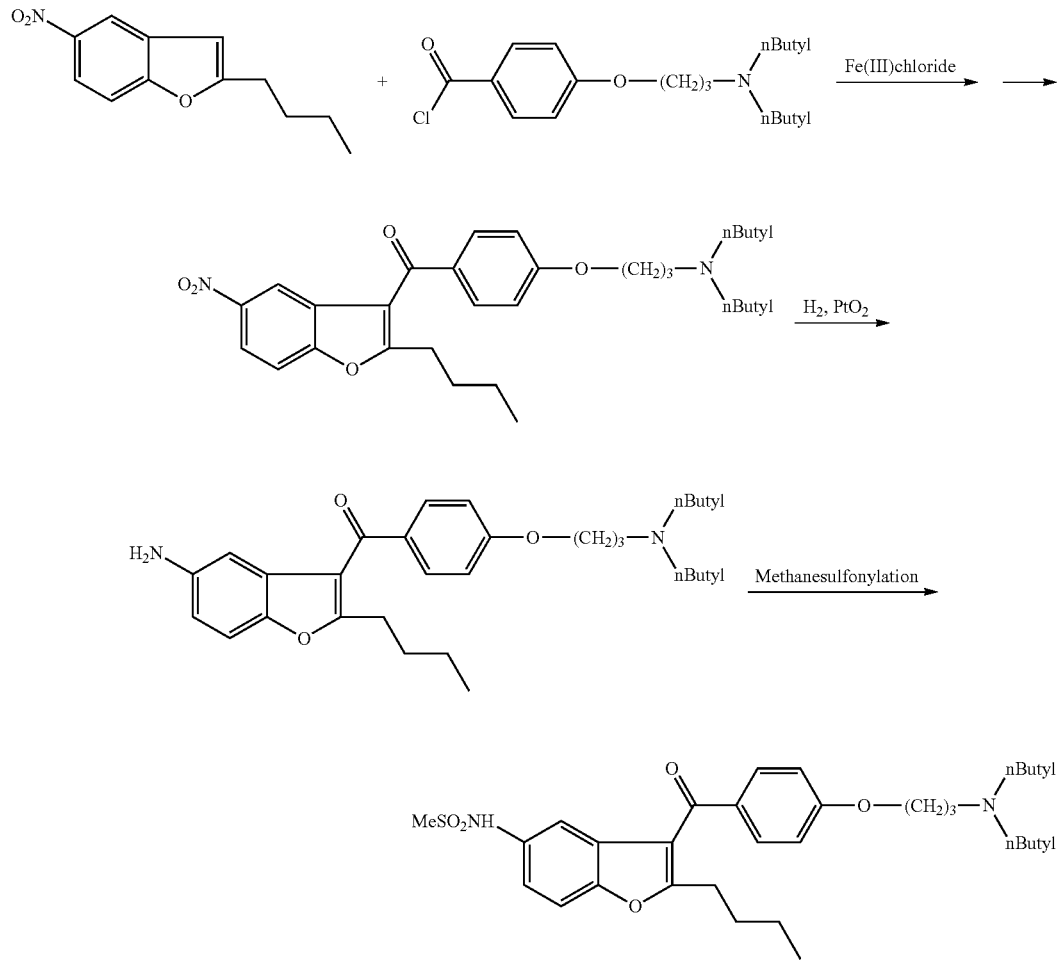

The novelty of the process is based on the adaptation of the Friedel-Crafts reaction in the first step. The process and the intermediary compounds used for the preparation of the benzoylchloride compound of the first step are also disclosed in this document. The further steps of the process are identical with the final steps of the synthetic route disclosed in EP 0471609 [Process A], but in the claims the whole synthetic route is claimed, up to dronedarone.

In WO 02/48132 (Sanofi) the following reaction route is disclosed [Process C]. This method is the so-called super-convergent route. In the first step of it 5-amino-2-butylbenzofuran

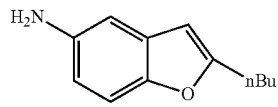

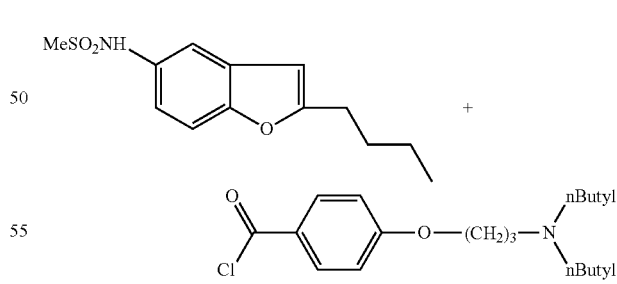

In this process the order of reaction steps are altered, the reduction and the methansulfonylation steps are performed at the beginning of the procedure. Besides the reaction route for preparation of dronedarone, the starting material 2-butyl-5-methansulfonamido-benzofuran and its preparation is also claimed.

From among the mentioned procedures the first one [Process A] is the so-called linear synthesis. In this way of procedure the different parts of the dronedarone are stepwise built up on the starting compound. This method is the least economical because the step by step building of the chemical groups is performed where more and more complicated and expensive molecules are applied which rises the costs of preparation. Furthermore, it comprises complicated and dangerous reaction step because aluminium chloride is used in the cleaving reaction of the methoxy group which makes the industrial feasibility more complicated.

In WO 02/48078 (Process B) a shorter synthetic route is disclosed which makes this process more economical, but its last reaction step remained, the methansulfonylation reaction of the amino group. This reaction step (see the method described in example 6 of WO 02/48078) is complicated and give a low yield, only 61.6%. Pure product can be obtained after purification using chromatographic column purification, which is necessary because of the separation difficulties of the bis-methanesulfonylated product.

The process disclosed in WO 02/48132 (process C) is simpler and more economical taken into consideration the number of the reaction steps. Unfortunately, in the last reaction step rather impure dronedarone. HCl (hydrochloride) is formed which is the obvious consequence of the presence of dibutylamino group in the Friedel-Crafts reaction. According to Examples 3 and 4, the crude dronedarone hydrochloride salt is prepared with a yield of 90% which was further purified and finally the crude dronedarone base was produced with a yield of 86%. This base is reacted with hydrogen chloride gas dissolved in isopropanol which results in pure dronedarone hydrochloride salt. No yield was given for this reaction step. According to example 5 crude dronedarone hydrochloride salt was prepared with a yield of 90%, which was washed with water and reacted with hydrogen chloride gas dissolved in isopropanol, resulting dronedarone hydrochloride salt again. The quality of this product is not known. However, neither the components used in the Friedel-Crafts reaction nor the resulted products and by-products are soluble in water, the washing step with water cannot result any purification apart from the removal of inorganic salts.

It is an object of present invention to provide a novel process for the preparation of dronedarone of formula (I). Starting with known and commercially available materials, applying simple and environmentally compatible reagents and solvents to afford high overall yields and good purity of the product.

SUMMARY OF THE INVENTION

The main aspect of the invention is a process for preparation of dronedarone (I) an pharmaceutically acceptable salts thereof (I)

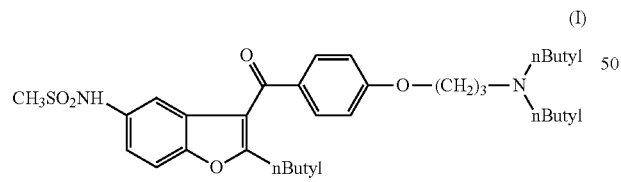

wherein from the compound of formula (II)

(II)

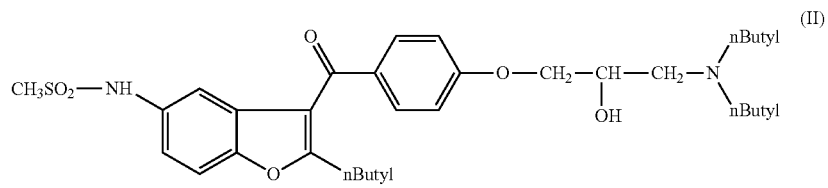

the hydroxyl group is removed.

The present invention avoids the drawbacks of the procedures mentioned before, because formation of dronedarone in the final step is completed by removing the hydroxyl group next to the dibutylamine. This type of reaction is advantageous because only little amounts of by-products are formed during the reduction process. The last step of the synthetic route can be performed with a good yield using this type of reaction and the purity of the product is also satisfactory. The reactants of this reaction are not expensive and are widely used in the chemical laboratory praxis.

Although removal of hydroxyl group from a compound is known in the chemical literature [Org. Synth. Coll, Vol. 1., 224 (1941); Jerry March: Advanced Organic Chemistry, Reactions, Mechanism and Structure, Chapter: Aliphatic Nucleofil Substitution, page 442 (4$^{th}$ edition, John Wiley & Sons)] there is no common method to use for removal of a hydroxyl group beside a tertiary amino group. We found that the beta-hydroxyl group can be removed with the described methods from the new compound of formula (II). The compound of formula (VII) is known from patent WO 02/48132 (Sanofi). The compounds of formula (VIII) are known and can be purchased from usual commercial sources.

Some intermediary compounds used in synthesis of dronedarone are new. Further aspects of the invention are the novel intermediary compounds and the methods for the preparation thereof (see below in the "Detailed description of the invention" part). The applied other starting materials are available from commercial sources.

DETAILED DESCRIPTION OF THE INVENTION

Therefore the present invention relates to a process for the preparation of dronedarone and pharmaceutically acceptable salts thereof. The whole process—starting from compounds available commercial sources—reads as follows:

A) For the preparation of compound of formula (V)

(V)

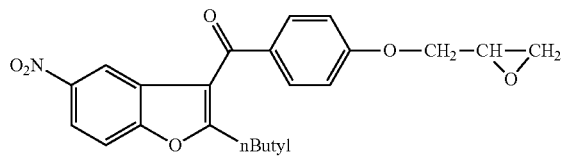

the compound of formula (VII)

(VII)

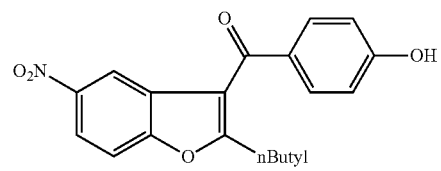

is reacted with a compound of formula (VIII)

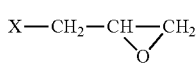
(VIII)

where X is halogen, typically chlorine.

The reaction is carried out in a solvent, or mixture of inert solvents, typically in the presence of base. The solvent can be selected from the group of C1-C4 alcohols (e.g. ethanol or isopropyl alcohol), ketones (e.g. methylethyl ketone) and acetonitril and mixtures thereof.

The base (applied for acid binding) can be selected from group of inorganic bases [e.g. carbonates, hydrogen carbonates (typically alkali carbonates), alkali hydroxides].

The temperature is typically between 50-120° C.

B) For the preparation of compound of formula (IV)

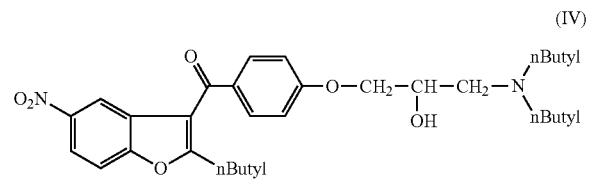
(IV)

the compound of formula (V)

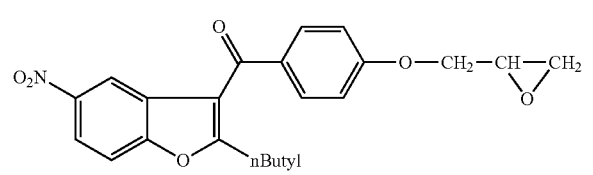
(V)

is reacted with the amine of formula (VI)

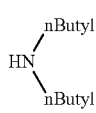
(VI)

Typically the reaction is carried out in a solvent. The solvent can be selected from the group C1-C4 alcohols, ethyl acetate and tetrahydrofurane and mixtures thereof (e.g. propanol or ethanol, especially propanol, e.g. isopropanol).

The temperature is typically between 50-120° C.

C) For the preparation of compound of formula (III) and pharmaceutically acceptable salts thereof

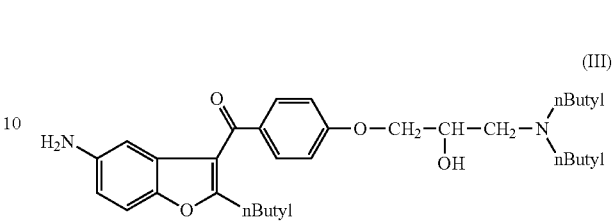
(III)

the compound of formula (IV)

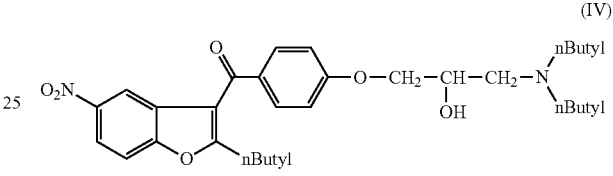
(IV)

is hydrogenated.

The hydrogenation of compound of formula (IV) is carried out in a solvent or mixture of solvents, in the presence of a catalyst, which can be e.g. $PtO_2$ or Pd/C. The solvent can be selected from the group C1-C4 alcohols, ethyl acetate, cyclohexane and tetrahydrofurane and mixtures thereof (e.g. ethanol or methanol).

D) For the preparation of compound of formula (II) and pharmaceutically acceptable salts thereof,

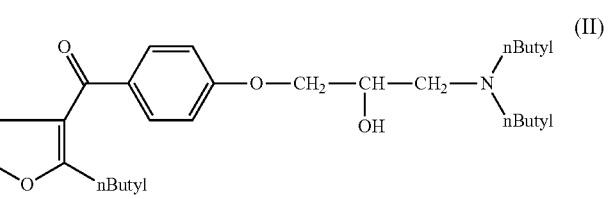
(II)

the compound of formula (III)

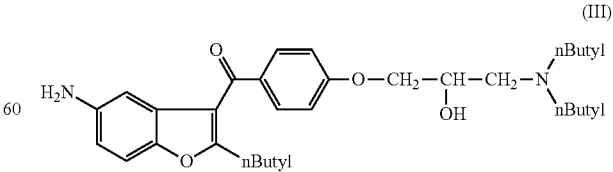
(III)

is mesylated.

The mesylation is carried out in a solvent or mixture of inert solvents, typically in the presence of base. The solvent can be selected from the group of halogenated solvents (e.g. dichloromethane, dichloroethane, chlorobenzene), aromatic solvents (e.g. toluene) and ethers (e.g. diisopropyl ether) and mixtures thereof. The base can be selected from group of tertiary amines (e.g. pyridine or triethyl amine) and inorganic bases (e.g carbonates, hydrogen carbonates, alkali hydroxides). In the process a mesylating reagent should be applied. It can be any reagent which can be used for inserting a $CH_3SO_2$— group into the free amino group of compound of formula (III). It is practical to use methanesulfonic anhydride or methanesulfonyl halogenide, e.g. methanesulfonyl chloride.

E) Finally, for the preparation of dronedarone of formula (I) and pharmaceutically acceptable salts thereof the boiling point of the applied solvent (which can be the mixture of the mentioned solvents in a specific embodiment). Applicable temperature values can be found in the examples.

All the above reactions are carried out under atmospheric pressure with the exception of the hydrogenation steps where higher pressure also can be applied, typically up to 20 bar, e.g. 5 to 10 bar. Applicable pressure values can be found in the examples.

The applicable acid for the preparation of pharmaceutically acceptable salts can be any inorganic or organic acid which forms an acid addition salt with the compound of general formula (I). Exemplary acids which can form an acid addition salt are as follows: acetic acid, adipic acid, alginic

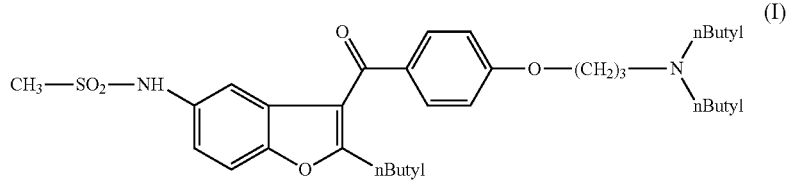

from the compound of formula (H)

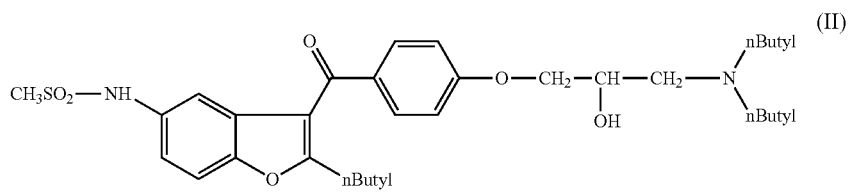

the hydroxyl group is removed.

The removal of hydroxyl group can be carried out by any usable method known in the chemical literature, as it was discussed at the end of the Summary of the Invention part.

For example, the reaction is carried out with reagent(s) selected from the following groups:
a) hydrogen iodide and phosphorous acid ($H_3PO_3$),
b) dialkyl silane and boron trifluoride,
c) sodium iodide and dihalogen(dialkyl)silane, e.g. dichlorodimethyl silane,
d) iodotrimethyl silane,
e) sodium borohydride and trifluoacetic acid,
f) phosphorus and iodine.

In a typical method the reaction is carried out with hydrogen iodide and phosphorous acid in acetic acid as solvent.

In another typical method the reaction is carried out with sodium iodide and dichlorodimethyl silane in acetonitrile as solvent.

As used herein, the term alkyl includes straight or branched aliphatic hydrocarbon chains of 1 to 6 carbon atoms, e.g., methyl, ethyl, isopropyl and t-butyl.

As used herein, the term "halogen" includes fluoro, chloro, bromo and iodo atoms.

In the above reactions the temperature is chosen according to the general practice of a person skilled in organic chemistry. Typically the temperature is between 10° C. and acid, ascorbic acid, aspartic acid, benzoic acid, benzenesulfonic acid, methansulfonic acid, ethansulfonic acid, boric acid, butyric acid, citric acid, fumaric acid, hydrogen chloride, hydrogen bromide, hydrogen iodide, 2-hydroxyethanesulfonic acid, maleic acid, oxalic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt.

Here it is mentioned that on the mesylate group of compound of general formula (I) (see the "left side" of the molecule) a salt formation can be carried out (on the amide part of it) by a strong base, e.g. an alkaline hydroxide, typically by sodium hydroxide. However, these salts have less practical. importance, but they are within the scope of salts. It means that the phrase "salts" embraces both the acid addition salts and the salts formed by bases (basic salts) in case of compounds of general formula (I).

As it was mentioned above the further starting materials are commercially available or can be prepared by applying known synthetic ways, e.g. as it is given in the relating examples.

Other objects of the invention are the novel intermediary compounds applied in the processes, namely the following compounds:

The compound of formula (II) and pharmaceutically acceptable salts thereof

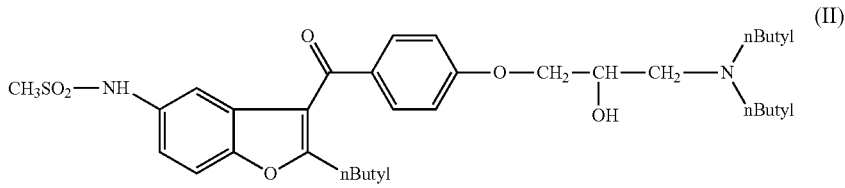

The compound of formula (III) and pharmaceutically acceptable salts thereof

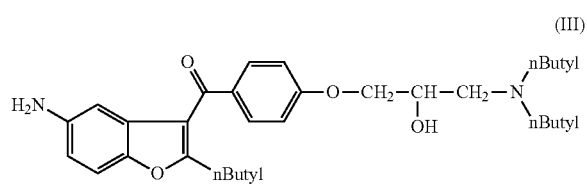

The compound of formula (IV) and pharmaceutically acceptable salts thereof

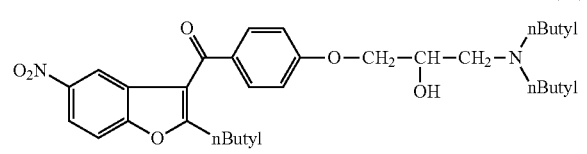

The compound of formula (V)

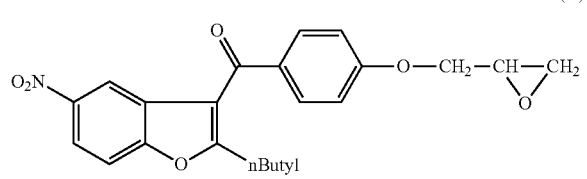

In the processes for the preparation of the intermediary compounds the product is isolated as a base typically (if the compound has an alkylated amino group). If desired, the isolated base can be converted into a salt (acid addition salt) thereof, which is typically a pharmaceutically acceptable salt [the possible acids are mentioned in point E)]. Theoretically the acid addition salt can be prepared directly if the relating acid is in the final reaction mixture from which the solid product is made (however, this way is not applied in case of these compounds where the base type form has practical importance).

Here it is mentioned that the above intermediary compound of formula (II) has a mesylate group (see the "left side" of the molecules) where a salt formation can be carried out (on the amide part of it) by a strong base, e.g. an alkaline hydroxide, typically by sodium hydroxide. However, these salts have less practical importance, but they are within the scope of salts which can be prepared by the claimed process, i.e. the phrase "salts" embraces the salts formed by bases (basic salts) in such cases (where the molecule has a mesylate group).

EXAMPLES

The solutions where the solvent is not defined are aqueous solutions in all the examples.

Example 1

N-[2-butyl-3-{4-[(3-dibutylamino)propoxy]benzoyl}-1-benzofuran-5-yl]-methanesulfonamide (I)

0.5 g of N-(2-butyl-3-(4-[3-(dibutylamino)-2-hydroxypropoxy]benzoyl}Ibenzofuran-5-yl)methanesulfonamide (II) 0.1 g of phosphorous acid ($H_3PO_3$) of 99% and 0.05 g of aqueous hydrogen iodide solution of 57% was dissolved in 5 ml of acetic acid. The mixture was warmed at 60 °C. for 1 hour and at 80 °C. for 4 hours. The mixture was cooled to 25 °C. and diluted with 10 ml of water. The pH was set to pH=7 using diluted sodium hydroxide. The mixture was extracted with 2×5 ml of dichloromethane. The dichloromethane was washed with 2×5 ml of water and evaporated.

Mass of product 0.48 g (98%). The product was purified by column chromatography on silica gel (eluent: ethyl acetate/hexane 1:3 v/v).

Mass of purified product: 0.44 g (90%).

Purity (HPLC): 99.44%.

1H NMR (DMSO): 0.8-0.9 ppm (m, 9H); 1.2-1.5 (m, 10H); 1.67 (5', 2H); 1.87 (5', 2H); 2.38 (t, J=7.2 Hz, 4H); 2.57 (m, 2H); 2.81 (t, J=7.5 Hz, 2H); 2.91 (s, 3H); 4.15 (t, J=6.2 Hz, 2H); 7.09 (d, J=8.8 Hz, 2H); 7.24 (dd, J=8.9, 2.2 Hz, 1H); 7.34 (d, J=2.1 Hz, 1H); 7.65 (d, J=8.8 Hz, 1H); 7.81 (d, J=8.8 Hz, 2H).

Example 2

N-[2-butyl-3-{4-[(3-dibutylamino)propoxy]benzoyl}-1-benzofuran-5-yl]-methanesulfonamide (I)

0.8 g of N-(2-butyl-3-{4-[3-(dibutylamino)-2-hydroxypropoxy]benzoyl}-1-benzofuran-5-yl)methanesulfonamide (II) was dissolved in 2 ml of acetonitrile and 0.9 g of sodium iodide was added. Under stirring at 25° C. 0.2 g of dichlorodimethylsilane was added. After stirring for 15 min the mixture was diluted with 5 ml of ethyl acetate and washed with 5 ml of water, with 5 ml of sodium hydrocarbonate solution of 5%, with sodium thiosulfate solution of 10% and with water. The solvent was evaporated. Mass of product 0.8 g.

The product is purified by forming its oxalate salt as follows: to the residue 4 ml of methylethyl ketone is added and the mixture heated to 70. To this solution 0.17 g of oxalic acid dissolved in 1.5 ml of methylethyl ketone is added at 70° C. After cooling to 20° C. in 6 hours the mixture is stirred at 10° C. for 1 hour and filtered. To the obtained oxalate salt 2.5 ml of water and 4 ml of dichloromethane and 0.46 g of potassium carbonate are added. After stirring for 30 minutes the separated potassium oxalate is filtered and washed with 2 ml of dichloromethane and the solvent is evaporated.

Mass of purified product 0.75 g (92%).
Purify (HPLC): 98.9%.
The product was identical with compound prepared in example 1.

Example 3

N-(2-butyl-3-{4-[3-(dibutylamino)-2-hydroxy-propoxy]benzoyl}-1-benzofuran-5-yl)-methane-sulfonamide (II)

0.3 g of (5-amino-2-butyl-1-benzofuran-3-yl){4-[3-(dibutylamino)-2-hydroxy-propoxy]-phenyl}methanone (III) was dissolved in 10 ml of dichloromethane. The solution was warmed to 30-35° C. and 0.06 g of pyridine was added at this temperature. After this 0.093 g of methanesulfonyl chloride was added and the mixture was stirred at 30-35° C. for 2 hours. The mixture was cooled to 20-25° C., washed with 2×15 ml of water, 2×15 ml of sodium hydrogencarbonate solution of 5%, 1×15 ml of water. The phases were separated and the dichloromethane phase was evaporated.

Mass of product: 0.32 g (94.1%).
Purity (HPLC): 78.9%.
$[M-H]^+_{measured}$=573.3 Da.
$[M-H]^+_{calculated}$=573.3 Da.
1H NMR (DMSO): δ ppm 0.78-0.87 (m,9 H) 1.18-1.31 (m, 6 H) 1.33-1.44 (m, 4H) 1.65 (quin, J=7.30 Hz, 2H) 2.28-2.49 (m, 5H) 2.59-2.68 (m, 1H) 2.79 (t, J=7.32 Hz, 2H) 2.89 (s, 3H) 3.86 (br. S, 1H) 3.97-4.06 (m, 1H) 4.12 (dd, J=9.84, 3.43 Hz, 1H) 7.08 (d, J=8.93 Hz, 2H) 7.22 (dd, J=8.81, 2.17 Hz, 1H) 7.32 (d, J=1.83 Hz, 1H) 7.62 (d, J=8.70 Hz, 1H) 7.79 (d, J=8.70 Hz, 2H).

Example 4

(5-amino-2-butyl-1-benzofuran-3-yl){4-[3-(dibutylamino)-2-hydroxypropoxy]-phenyl}-methanone (III)

2.2 g of (2-butyl-5-nitro-1-benzofuran-3-yl){[3-(dibutylamino)-2-hydroxypropoxy]-phenyl}ethanone (IV) was dissolved in 32 ml of methanol and 0.7 g of Pd/C catalyst of 5% was added. The mixture was set under hydrogen pressure of 10 bar and stirred at 25° C. for 90 min. The catalyst was filtered off and the solution was evaporated.

Mass of product: 1.9 g (92.7%).
Purity (HPLC): 92.1%.
$[M-H]^+_{measured}$=495.3 Da.
$[M-H]^+_{calculated}$=495.3 Da.
1H NMR (DMSO): δ ppm 0.80 (t, J=7.30 Hz, 3 H) 0.83 (t, J=7.32 Hz, 6 H) 1.23-1.28 (m, 6H) 1.34-1.37 (m, 4H) 1.62 (quin, J=7.50 Hz, 2H) 2.34-2.42 (m, 5H) 2.5'8 (dd, J=13.05, 7.55 Hz, 1H) 2.71 (t, J=7.55 Hz, 2H) 3.84-3.92 (m, 1H) 3.99 (dd, J=9.84, 5.72 Hz, 1H) 4.11 (dd, J=9.96, 3.09 Hz, 1H) 6.53 (d, J=2.06 Hz, 1H) 6.58 (dd, J=8.70, 2.29 Hz, 1H) 7.07 (d, J=8.70 Hz, 2 III) 7.26 (d, J=8.70 Hz, 1H) 7.75 (d, j=8.93 Hz, 2H).

Example 5

(2-butyl-5-nitro-1-benzofuran-3-yl){[3-(dibutylamino)-2-hydroxypropoxy]-phenyl}methanone (IV)

1.4 g of (2-butyl-5-nitro-1-benzofuran-3-yl)[4-(oxiran-2-yl-methoxy)phenyl]-methanone (V) was dissolved in 10 ml of isopropanol. 2.74 g of dibutylamin was added and the mixture was boiled for 4 hours. The mixture was evaporated.

Mass of product: 1.88 g (100%).
Purity (HPLC): 92.0%.
$[M-H]^+_{measured}$=525.3 Da.
$[M-H]^+_{calculated}$=525.3 Da.

1H NMR (DMSO): 0.78-0.84 ppm (m, 9H); 1.20-1.29 (m, 6H); 1.30-1.38 (m, 4H); 1.68 (quin, J=7.5 Hz, 2H); 2.37-2.46 (m, 5H); 2.58 (dd, J=13.05, 7.78 Hz, 1H); 2.84 (t, J=7.55 Hz, 2H); 3.85-3.91 (m, 1H); 4.02 (dd, J=9.96, 5.61 Hz, 1H); 4.13 (dd, J=9.84, 3.20 Hz, 1H); 7.10 (d, J=8.93 Hz, 2H); 7.82 (d, J=8.93 Hz, 2H); 7.92 (d, J=8.24 Hz, 1H); 8.23-8.28 (m, 2H).

Example 6

(2-butyl-5-nitro-1-benzofuran-3-yl)[4-(oxiran-2-yl-methoxy)phenyl]methanone (V)

5 g of (2-butyl-5-nitro-1-benzofuran-3-yl)(4-hydroxyphenyl)methanone (VII) was dissolved in 30 ml of acetonitrile and 6.1 g of potassium carbonate, 6.6 g of sodium iodide and 4.0 g of epichlorohydrin were added. The mixture was boiled for 6 hours and cooled down. The solid was filtered off and the solution was evaporated.

Mass of product: 5.9 g (101%).
Purity (HPLC): 87.9%.
$[M-H]^+_{measured}$=396.1 Da.
$[M-H]^+_{calculated}$=396.1 Da.
1H NMR (DMSO): 0.81 ppm (t, J=7.32 Hz, 3H); 1.25 (sxt, J=7.30 Hz, 2H); 1.68 (quin, J=7.44 Hz, 2H); 2.75 (dd, J=5.04, 2.52 Hz, 1H); 2.84 (t, J=7.55 Hz, 2H); 2.86-2.89 (m, 1H); 3.33-3.39 (m, 1H); 3.94-4.00 (m, 1H); 4.49 (dd, J=11.22, 2.75 Hz, 1H); 7.10-7.18 (m, 2H); 7.83 (dd, J=8.70, 2.75 Hz, 1H); 7.92 (d, J=9.84 Hz, 1H); 8.22-8.28 (m, 2H).

Example 7

(2-butyl-5-nitro-1-benzofuran-3-yl)[4-(oxiran-2-yl-methoxy)phenyl]methanone (V)

5 g of (2-butyl-5-nitro-1-benzofuran-3-yl)(4-hydroxyphenyl)methanone (VII) was dissolved in 50 ml of isopropanol and 0.625 g of solid sodium hydroxide was added. The mixture was stirred at room temperature for 10 min and 2.5 g of epibromohydrine (VIII) (Aldrich) was added. The mixture was boiled for 90 min and evaporated at 40° C. 15 ml, of water of 0° C. was added and 30 ml of dichloromethane. The phases were separated after 10 min of stirring. The dichloromethane was evaporated.

Mass of product: 5.85 g (100%).
Purity (HPLC): 90.1%.
$[M-H]^+_{measured}$=396.1 Da.
$[M-H]^+_{calculated}$=396.1 Da.
The product was identical with compound prepared in example 6.

The invention claimed is:
1. The compound of formula (II) or a pharmaceutically acceptable salt thereof

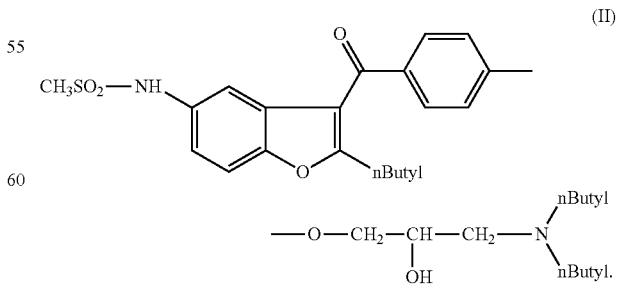

2. A process for the preparation of the compound of formula (II) or a pharmaceutically acceptable salt thereof,

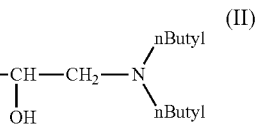

comprising the steps of:

a) reacting the compound of formula (III)

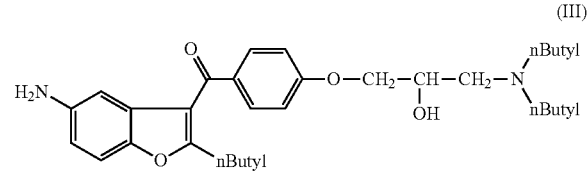

with a mesylating reagent to generate the compound of formula (II), b) separating the compound of formula (II) generated in a step a), and c) optionally reacting the compound of formula (II) separated in step b) with a pharmaceutically acceptable inorganic acid to generate a pharmaceutically acceptable salt of the compound of formula (II).

3. The process of claim 2, wherein the mesylating reagent is methanesulfonic anhydride or methanesulfonyl halogenide.

4. The process of claim 3, wherein the mesylating reagent is methanesulfonyl chloride.

* * * * *

UNITED STATES PATENT AND TRADEMARK OFFICE
CERTIFICATE OF CORRECTION

PATENT NO. : 9,701,654 B2
APPLICATION NO. : 14/946510
DATED : July 11, 2017
INVENTOR(S) : Antal Friesz et al.

Page 1 of 2

It is certified that error appears in the above-identified patent and that said Letters Patent is hereby corrected as shown below:

On the Title Page

Page 2, Section "OTHER PUBLICATIONS", right-hand side column, Line 51 of this column: please replace "Desmethyiated" with --Desmethylated--; and Page 2, Section "OTHER PUBLICATIONS", right-hand side column, Line 57 of this column: please replace "Gutowski et al," with --Gutowski et al.--.

In the Claims

At Column 14, Claim number 1, Line numbers 52-65: please replace the chemical structure " 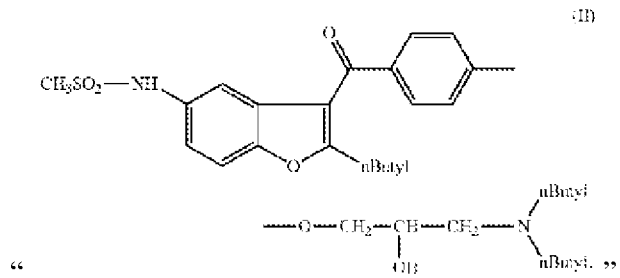 "

with -- 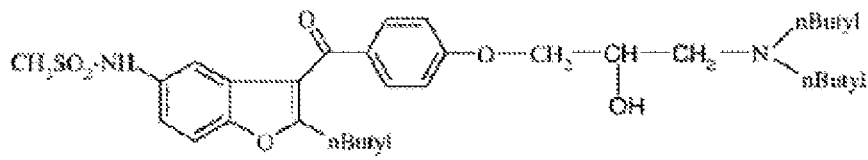 --;

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,701,654 B2

At Column 16, Claim number 2, Line number 14: please replace "a step a), and" with --step a), and--; and At Column 16, Claim number 2, Line number 17: please replace "inorganic acid" with --inorganic or organic acid--.